United States Patent [19]
Kim et al.

[11] Patent Number: 5,998,644
[45] Date of Patent: Dec. 7, 1999

[54] VOLATILE ORGANOMETALLIC COMPOUND CONTAINING A DIVALENT METAL AND A GROUP 13 METAL, PROCESS FOR PREPARING SAME, AND PROCESS FOR PREPARING A HETEROMETALLIC OXIDE FILM USING SAME

[75] Inventors: Yun-Soo Kim; Won-Yong Koh; Su-Jin Ku; Chang-Gyoun Kim; Kyu-Sang Yu, all of Daejeon, Rep. of Korea

[73] Assignee: Korea Research Institute of Chemical Technology, Rep. of Korea

[21] Appl. No.: 09/132,523

[22] Filed: Aug. 11, 1998

[30] Foreign Application Priority Data

Aug. 12, 1997 [KR] Rep. of Korea ...................... 97-38384

[51] Int. Cl.$^6$ ................. C07F 19/00; C07F 5/06
[52] U.S. Cl. ................. 556/28; 556/1; 556/27; 556/181; 556/182; 427/248.1
[58] Field of Search .................. 556/27, 28, 1, 556/181, 182

[56] References Cited

U.S. PATENT DOCUMENTS 5,008,420  4/1991  Greco et al. ............................ 556/182

Primary Examiner—Porfirio Nazario-Gonzalez
Attorney, Agent, or Firm—Anderson Kill & Olick

[57] ABSTRACT

A novel organometallic compound of formula $M[(\mu\text{-}OR')_2M'R_2]_2$ can be vaporized at a low temperature and advantageously employed in the CVD of a heterometallic oxide film of the $MM'_2O_4$ type, wherein M is a divalent element such as Be, Mg, Zn or Cd; M' is a Group 13 element such as Al or Ga; and R and R' are each independently a $C_{1\text{-}10}$ alkyl group, with the proviso that if M is Mg, M' is not Al.

4 Claims, 1 Drawing Sheet

VOLATILE ORGANOMETALLIC COMPOUND CONTAINING A DIVALENT METAL AND A GROUP 13 METAL, PROCESS FOR PREPARING SAME, AND PROCESS FOR PREPARING A HETEROMETALLIC OXIDE FILM USING SAME

FIELD OF THE INVENTION

The present invention relates to a volatile organometallic compound of formula $M[(\mu OR')_2M'R_2]_2$ wherein M and M' are a divalent metal and a Group 13 metal, respectively, with R and R' each being an alkyl group. The present invention also relates to a chemical vapor deposition (CVD) process for depositing an $MM'_2O_4$ type heterometallic oxide film on a substrate using the organometallic compound.

BACKGROUND OF THE INVENTION

A heterometallic oxide film of the $MM'_2O_4$ type, wherein M is a divalent metal and M' is a Group 13 metal, is a very useful material in the electronics field. For instance, $ZnGa_2O_4$ is used as a low voltage phosphor material for a flat panel display device (see I. J. Hsieh et al., *Journal of Applied Physics*, 76, 3735–3739(1994); L. E. Shea et al., *Journal of Electrochemical Society*, 141, 2198–2200(1994); and U.S. Pat. No. 5,558,814); $CdGa_2O_4$ and $ZnGa_2O_4$ are promising materials for applications as a transparent electroconductive material (see T. Omata, N. Ueda, N. Hikuma, K. Ueda, H. Mizoguchi, T. Hashimoto, and H. Kawazoe, "New oxide phase with wide band gap and high electroconductivity $CdGa_2O_4$ spinel", *Applied Physics Letters*, 62(5), 499(1993); T. Omata, N. Ueda, K. Ueda and H. Kawazoe, "New ultraviolet transport electroconductive oxide, $ZnGa_2O_4$ spinel", *Applied Physics Letters*, 64(9), 1077 (1994)); $CaGa_2O_4$ and $CaAl_2O_4$ are widely used as a fluorescent material (U.S. Pat. Nos. 5,424,006and 5,725, 801); and a single crystal of $BeAl_2O_4$ is used as a laser material when doped with chromium(see U.S. Pat. No. 5,090,019). Some of these heterometallic oxides are usually prepared in a powder form from simple oxides of constitutive elements. For example, $ZnGa_{2\ 4}$ powder is synthesized from a powder mixture of ZnO and $Ga_2O_3$. However, it is difficult to prepare a high purity complex oxide, in addition to the handling difficulties in fabricating an electronic device using a high surface area powder.

Accordingly, a CVD process has been attempted in the preparation of an $MM'_2O_4$ type oxide using vaporizable alkoxide precursors such as magnesium aluminum isopropoxide of formula $Mg[Al(OPr^i)_4]_2$. However, it has been reported that this type of alkoxide precursors are prone to undergo disproportionation reactions to form higher molecular weight compounds, e.g., $Mg_2Al_3(OPr^i)_{13}$ (see J. A. Meese-Marktscheffel et al., *Chemistry of Materials*, 5, 755–757 (1993)). The formation of such high molecular weight compounds causes the problem of lowering the vapor pressure of the precursor during the CVD process.

Accordingly, there has existed a need to develop a simple, efficient process for the preparation of a high purity heterometallic oxide film of the $MM'_2O_4$ type.

SUMMARY OF THE INVENTION

It is, therefore, an object of the present invention to provide a novel organometallic compound which can be advantageously used in a CVD process for depositing a heterometallic oxide film of the $MM'_2O_4$ type.

It is another object of the present invention to present an improved process for the preparation of said organometallic compound.

It is a further object of the present invention to offer a process for the deposition of a heterometallic oxide film of the $MM'_2O_4$ type on a substrate using said organometallic compound.

In accordance with one aspect of the present invention, there is provided a volatile organometallic compound of formula $M[(\mu\text{-}OR')_2M'R_2]_2$ wherein M is a divalent element such as Be, Mg, Zn or Cd; M' is a Group 13 element such as Al or Ga; and R and R' are each independently a $C_{1-10}$ alkyl group, with the proviso that if M is Mg, M' is not Al.

In accordance with another aspect of the present invention, there is presented a process for preparing a volatile organometallic compound of formula $M[(\mu\text{-}OR')_2M'R_2]_2$ wherein M is a divalent element such as Be, Mg, Zn or Cd; M' is a Group 13 element such as Al or Ga; and R and R' are each independently a $C_{1-10}$ alkyl group, with the proviso that if M is Mg, M' is not Al, which comprises: (i) reacting an alkyl compound of Group 13 element of formula $R_3M'$ with an alcohol (R'OH) or with an alkoxide of the same element of formula $M'(OR')_3$ to obtain a dialkylmetal alkoxide of formula $R_2M',OR'$; (ii) reacting the dialkylmetal alkoxide with an alkali metal alkoxide of formula M"OR', wherein M" is an alkali metal such as Li, Na or K to obtain an alkali metal dialkylmetal alkoxide of formula $M''(\mu\text{-}OR')_2M'R_2$; (iii) reacting the alkali metal dialkylmetal alkoxide with a divalent metal halide of formula $MX_2$, wherein X is Cl, Br or I; and (iv) isolating the volatile organometallic compound.

In accordance with a further aspect of the present invention, there is disclosed a process for coating a substrate with a heterometallic oxide film of the $MM'_2O_4$ type, which comprises bringing the vapor of a volatile organometallic compound of formula $M[(\mu\text{-}OR')_2M'R_2]_2$ into contact with the substrate heated to a temperature above 300° C., wherein M is a divalent element such as Be, Mg, Zn or Cd; M' is a Group 13 element such as Al or Ga; and R and R' are each independently a $C_{1-10}$ alkyl group, with the proviso that if M is Mg, M' is not Al.

BRIEF DESCRIPTION OF THE DRAWING

The above and other objects and features of the present invention will become apparent from the following description of the invention, when taken in conjunction with the accompanying drawing, in which.

DETAILED DESCRIPTION OF THE INVENTION

Figure 1:
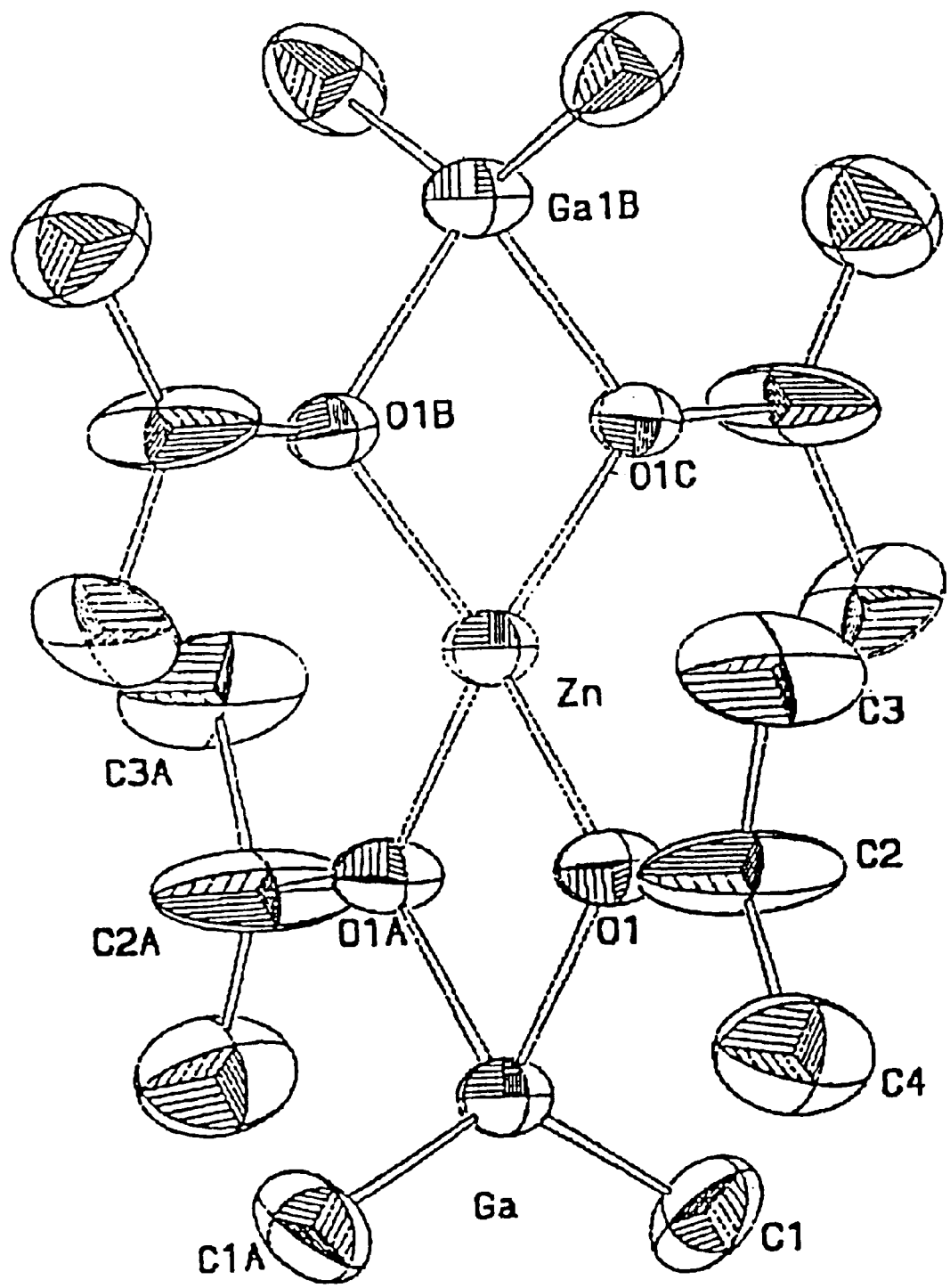
FIG. 1 shows the structure of zinc dimethylgallium isopropoxide $(Zn[(\mu\text{-}OPr^i)_2GaMe_2]_2)$ crystal determined by X-ray crystallography.

The novel organometallic compound of the present invention is a highly volatile compound of formula $M[(\mu\text{-}OR')_2M'R_2]_2$ which has an M:M':O atomic ratio of 1:2:4. It can be, therefore, advantageously used in a CVD process for depositing an $MM'_2O_4$ type heterometallic oxide film on a substrate. In the inventive organometallic compound of formula $M[(\mu\text{-}OR')_2M'R_2]_2$, M is a divalent element such as Be, Mg, Zn or Cd; M' is a Group 13 element such as Al or Ga; and R and R' are each independently a $C_{1-10}$ alkyl group, with the proviso that if M is Mg, M' is not Al. The most preferred in practicing the present invention are: beryllium dimethylaluminum isopropoxide, Be $[(\mu\text{-}OPr^i)_2AlMe_2]_2$; zinc dimethylgallium isopropoxide, Zn $[(\mu\text{-}OPr^i)_2GaMe_2]_2$; zinc diethylaluminum isopropoxide, Zn $[(\mu\text{-}OPr^i)_2AlEt_2]_2$; and cadmium dimethylaluminum tert-butoxide, Cd $[(\mu\text{-}OBu^t)_2AlMe_2]_2$.

The organometallic compound of the present invention may be prepared by the following procedure: (i) an alkyl compound of a Group 13 element($R_3M'$) is reacted with an alcohol (R'OH) or an alkoxide of the same element ($M'(OR')_3$) to obtain a dialkylmetal alkoxide ($R_2M'OR'$); (ii) the dialkylmetal alkoxide is reacted with an alkali metal alkoxide (M"OR' wherein M" is an alkali metal such as Li, Na or K) to obtain an alkali metal dialkylmetal alkoxide ($M''(\mu\text{-}OR')_2M'R_2$); and (iii) the alkali metal dialkylmetal alkoxide is reacted with a divalent metal halide ($MX_2$) to obtain the desired product. The above reaction steps may be shown as follows:

$$R_3M' + R'OH \rightarrow R_2M'OR' + RH \text{ or} \qquad (i)$$
$$2\,R_3M' + M'(OR')_3 \rightarrow 3\,R_2M'OR'$$

$$R_2M'OR' + M''OR' \rightarrow M''(\mu\text{-}OR')_2M'R_2 \qquad (ii)$$

$$2\,M''(\mu\text{-}OR')_2M'R_2 + MX_2 \rightarrow M[(\mu\text{-}OR')_2M'R_2]_2 + 2\,M''X \qquad (iii)$$

wherein:

R and R' are each independently a $C_{1\text{-}10}$ alkyl group;

M represents a divalent element such as Be, Mg, Zn or Cd;

M' represents a Group 13 element such as Al or Ga;

M" represents an alkali metal such as Li, Na or K; and

X represents Cl, Br or I.

In step (i), the alkyl compound of a Group 13 element may be reacted with either the alcohol in an equivalent ratio at a low temperature ranging from −20° C. to room temperature, or with the alkoxide of the same element in a molar ratio of 2:1 at room temperature. Further, in step (ii), the dialkylmetal alkoxide and the alkali metal alkoxide may be employed in an equivalent ratio, and in step (iii), the alkali metal dialkylmetal alkoxide and the divalent metal halide may be employed in a molar ratio of 2:1 at room temperature.

Either of the reactions in step (i) may be conducted without a solvent, while the reaction in step (ii) or (iii) may be carried out in an organic solvent such as diethyl ether, tetrahydrofuran or n-hexane, preferably under a nitrogen or argon atmosphere.

Alternatively, the dialkylmetal alkoxide obtained in step (i) may be directly reacted with a divalent metal alkoxide ($M(OR')_2$) in a molar ratio of 2:1 to obtain the desired product, as shown below:

$$2R_2M'OR' + M(OR')_2 \rightarrow M[(\mu\text{-}OR')_2M'R_2]_2$$

wherein M, M', R and R' have the same meanings as defined above.

The organometallic compound prepared in accordance with the present invention may be preferably vaporized at a temperature ranging from room temperature to 100° C.

A heterometallic oxide film of the $MM'_2O_4$ type may be deposited on a substrate by bringing the vapor of the inventive organometallic compound thus obtained into contact with the surface of a substrate preheated to a temperature above 300° C. under a pressure of $1 \times 10^{-5}$ to $1 \times 10^{-1}$ Torr, preferably under a pressure ranging from $1.5 \times 10^{-5}$ to $1.2 \times 10^{-2}$ Torr. The thermal decomposition of the inventive organometallic compound presumably occurs via a pathway involving a β-hydrogen abstraction step, and the organic moieties thereof are converted cleanly to an equimolar mixture of an alkane and an olefin, leaving a minimal amount of residual carbon in the deposited oxide film. For example, beryllium dimethylalumium isopropoxide undergoes a thermal reaction to give an equimolar mixture of methane and propylene as a gaseous by-product, while depositing a clean $BeAl_2O_4$ film containing little carbon.

The substrate which may be used in practicing the present invention is any inorganic solid which is stable at or above the film deposition temperature, and examples thereof include glass, quartz, silicon, gallium arsenide, sapphire, alkali metal niobate, alkaline earth metal titanate, gallium nitride, niobium nitride and the like, among which single crystals of silicon, glass, gallium arsenide and sapphire are preferred when the coated substrate is intended for use in electronic applications.

The following Examples are provided only for the purpose of illustrating certain aspects of the present invention; they are not to be construed as limiting the scope of the present invention in any way.

In each of Examples, the coated substrate obtained after treatment with the inventive organometallic compound was immediately transferred to an X-ray photoelectron spectroscope in order to minimize the exposure thereof to air.

Preparation of Organometallic Compounds

Example 1: Synthesis of beryllium dimethylaluminum isopropoxide, $Be[(\mu\text{-}OPr^i)_2AlMe_2]_2$ 0.72 g (10.9 mmol) of lithium isopropoxide was added to 1.27 g (10.9 mmol) of dimethylaluminum isopropoxide dissolved in diethyl ether and stirred for a day. 0.44 g (5.5 mmol) of beryllium chloride was then added thereto. The resulting mixture was stirred for a day and filtered.

The filtrate thus obtained was distilled under a reduced pressure to remove the solvent and the solid residue was sublimed under a vacuum at 70° C to obtain 1.01 g (2.81 mmol; yield of 52%) of the title compound in the form of a white solid.

$^1$H NMR analysis in benzene-$d_6$ of the compound thus obtained showed peaks at δ−0.41(singlet, $Al(CH_3)_2$, 12H), 1.13 (doublet, $OCH(CH_3)_2$, 24H) and 4.00(septet, OCH $(CH_3)_2$, 4H).

The X-ray photoelectron spectroscopic analysis of the compound thus obtained using ESCALAB MK II spectrometer (VG Scientific Ltd.) showed peaks corresponding to beryllium, aluminum, oxygen and carbon. The elemental composition of the compound (frozen at liquid nitrogen temperature) determined by comparing the photoelectron peak areas corresponded to a Be:Al:O:C atomic ratio of 1:2.01:4.78:16.59.

The compound thus obtained had a melting point of 56° C. and a vapor pressure of $1.00–1.10 \times 10^{-1}$ Torr at 31° C.

Example 2: Synthesis of zinc dimethylgallium isopropoxide, $Zn[(\mu\text{-}OPr^i)_2GaMe_2]_2$ 0.44 g (5.4 mmol) of sodium isopropoxide was added to 0.86 g (5.4 mmol) of dimethylgallium isopropoxide dissolved in diethyl ether and stirred for a day. 0.37 g (2.7 mmol) of zinc chloride was then added thereto. The resulting mixture was stirred for a day and filtered.

The filtrate thus obtained was distilled under a reduced pressure to remove the solvent and the solid residue was sublimed under a vacuum at 50° C. to obtain 0.95 g (1.9 mmol; yield of 70%) of the title compound in the form of a white solid.

The compound thus obtained had a melting point of 83° C.

$^1$H NMR analysis in benzene-d$_6$ of the compound thus obtained showed peaks at δ–0.05(singlet, Ga(CH$_3$)$_2$, 12H), 1.13 (doublet, OCH(CH$_3$)$_2$, 24H) and 4.04 (septet, OCH (CH$_3$)$_2$, 4H).

Example 3: Synthesis of zinc diethylaluminum isopropoxide, Zn[(μ-OPr$^i$)$_2$AlEt$_2$]$_2$ 0.74 g (5.5 mmol) of zinc chloride was slowly added to 2.30 g (10.9 mmol) of lithium diethylaluminum isopropoxide dissolved in diethyl ether. The resulting mixture was stirred for a day and filtered.

The filtrate thus obtained was distilled under a reduced pressure to remove the solvent and the solid residue was sublimed under a vacuum at 50° C. to obtain 1.18 g (2.50 mmol; yield of 45%) of the title compound in the form of a white solid.

Example 4: Synthesis of cadmium dimethylaluminum tert-butoxide, Cd[(μ-OBu$^t$)$_2$AlMe$_2$]$_2$ 2.55 g (13.9 mmol) of cadmium chloride was slowly added to 5.84 g (27.8 mmol) of lithium dimethylaluminum tert-butoxide dissolved in tetrahydrofuran. The resulting mixture was stirred for 6 hours and filtered.

The filtrate thus obtained was distilled under a reduced pressure to remove the solvent and the solid residue was sublimed under a vacuum at 50° C. to obtain 3.4 g (6.56 mmol; yield of 47%) of the title compound in the form of a white solid.

The compound thus obtained has a vapor pressure of 1.25–1.30 ×10$^{-1}$ Torr at 32° C.

Deposition of Heterometallic Oxide Films

Example 5

The compound prepared in Example 1 was vaporized at 60° C. and the vapor thereof was conveyed to a Si (100) substrate preheated to 400° C. for 1 hour and 40 minutes to deposit a film thereon. The X-ray photoelectron spectrum of the deposited film showed only the peaks corresponding to beryllium, aluminum, oxygen and carbon. The elemental composition of the film surface determined by comparing the photoelectron peak areas corresponded to a Be:Al:O atomic ratio of 1.0:2.3:5.6.

Example 6

The compound prepared in Example 1 was vaporized at 60° C. and the vapor thereof was conveyed to a Si (100) substrate preheated to 400° C. for 1 hour and 15 minutes to deposit a film thereon. The X-ray photoelectron spectrum of the deposited film showed only the peaks corresponding to beryllium, aluminum, oxygen and carbon. The elemental composition of the film surface determined by comparing the photoelectron peak areas corresponded to a Be:Al:O atomic ratio of 1.0:2.2:6.0.

Gaseous by-products evolved during the above CVD process were analyzed to be an equimolar mixture of methane and propylene. Thus, the thermal decomposition of beryllium dimethylaluminum isopropoxide proceeds via a pathway that cleanly removes the organic moieties as an alkane/olefin mixture.

Example 7

The compound prepared in Example 2 was vaporized at room temperature and the vapor thereof was conveyed to a Si (100) substrate preheated to 600° C. for 4 hours to deposit a film thereon. The X-ray photoelectron spectrum of the deposited film showed only the peaks corresponding to zinc, gallium, oxygen and carbon. The elemental composition of the film surface determined by comparing the photoelectron peak areas corresponded to a Zn:Ga:O atomic ratio of 1.0:2.4:6.6.

Example 8

The compound prepared in Example 2 was vaporized at room temperature and the vapor thereof was conveyed to a Si (100) substrate preheated to 400° C. for 6 hours to deposit a film thereon. The X-ray photoelectron spectrum of the deposited film showed only the peaks corresponding to zinc, gallium, oxygen and carbon. The elemental composition of the film surface determined by comparing the photoelectron peak areas corresponded to a Zn:Ga:O atomic ratio of 1.0:1.8:5.2.

Example 9

The compound prepared in Example 4 was vaporized at room temperature and the vapor thereof was conveyed to a Si (100) substrate preheated to 400° C. for 5 hours to deposit a film thereon. The X-ray photoelectron spectrum of the deposited film showed only the peaks corresponding to cadmium, aluminum, oxygen and carbon. The elemental composition of the film surface determined by comparing the photoelectron peak areas corresponded to a Cd:Al:O atomic ratio of 1.0:2.4:5.8.

As shown above, the organometallic compound having the formula of M[(μ-OR')$_2$M'R$_2$]$_2$ of the present invention can be vaporized at a temperature ranging from room temperature to 100° C., and therefore, it may be advantageously employed in the CVD of an MM'$_2$O$_4$ type heterometallic oxide film. In addition, the organometallic compound of the present invention may be used in the production of an MM'$_2$O$_4$ type heterometallic oxide powder and in the chemical vapor infiltration (CVI) of porous materials.

While the invention has been described with respect to the specific embodiments, it should be recognized that various modifications and changes may be made by those skilled in the art to the invention which also fall within the scope of the invention as defined by the appended claims.

We claim:

1. A volatile organometallic compound of formula M[(μ-OR')$_2$M'R$_2$]$_2$: wherein M is a divalent element; M' is a Group 13 element; and R and R' are each independently a C$_{1-10}$ alkyl group, with the proviso that if M is Mg, M' is not Al.

2. The organometallic compound of claim 1, wherein the divalent element is Be, Mg, Zn or Cd.

3. The organometallic compound of claim 1, wherein the Group 13 element is Al or Ga.

4. The organometallic compound of claim 1, which is beryllium dimethylaluminum isopropoxide, zinc dimethylgallium isopropoxide, zinc diethylaluminum isopropoxide or cadmium dimethylaluminum tert-butoxide.

* * * * *